United States Patent
Wendlandt

(10) Patent No.: US 8,882,656 B2
(45) Date of Patent: *Nov. 11, 2014

(54) DIAGNOSTIC CATHETER USING A VACUUM FOR TISSUE POSITIONING

(75) Inventor: Jeffrey M. Wendlandt, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2199 days.

This patent is subject to a terminal disclaimer.

(21) Appl. No.: 10/771,345

(22) Filed: Feb. 5, 2004

(65) Prior Publication Data

US 2004/0162485 A1 Aug. 19, 2004

Related U.S. Application Data

(63) Continuation of application No. 09/513,076, filed on Feb. 25, 2000, now Pat. No. 6,728,565.

(51) Int. Cl.
- *A61B 1/04* (2006.01)
- *A61B 1/00* (2006.01)
- *A61B 1/018* (2006.01)
- *A61B 1/015* (2006.01)
- *A61B 17/30* (2006.01)

(52) U.S. Cl.
CPC ....... *A61B 1/00094* (2013.01); *A61B 2017/306* (2013.01); *A61B 1/018* (2013.01); *A61B 1/015* (2013.01)
USPC ........... 600/112; 600/106; 600/407; 600/423; 606/15

(58) Field of Classification Search
CPC .................. A61B 2017/306; A61B 2018/306; A61M 2025/0681
USPC ....................... 600/407, 423, 106, 112; 606/15
See application file for complete search history.

(56) References Cited

U.S. PATENT DOCUMENTS

| | | | |
|---|---|---|---|
| 4,355,643 A | 10/1982 | Laughlin et al. | |
| 4,736,749 A | 4/1988 | Lundback | |
| 4,813,422 A * | 3/1989 | Fisher et al. | 600/473 |
| 4,832,048 A | 5/1989 | Cohen | |
| 5,105,819 A | 4/1992 | Wollschläger et al. | |
| 5,295,484 A * | 3/1994 | Marcus et al. | 600/439 |
| 5,299,560 A * | 4/1994 | Hatori | 600/121 |
| 5,307,816 A * | 5/1994 | Hashimoto et al. | 600/439 |
| 5,409,012 A | 4/1995 | Sahatjian | |
| 5,448,990 A * | 9/1995 | De Faria-Correa | 600/129 |
| 5,484,391 A | 1/1996 | Buckman, Jr. et al. | |
| 5,505,710 A | 4/1996 | Dorsey, III | |
| 5,509,900 A | 4/1996 | Kirkman | |
| 5,575,772 A | 11/1996 | Lennox | |
| 5,715,825 A * | 2/1998 | Crowley | 600/462 |

(Continued)

*Primary Examiner* — Sanjay Cattungal
*Assistant Examiner* — Ellsworth Weatherby
(74) *Attorney, Agent, or Firm* — Bookoff McAndrews, PLLC

(57) ABSTRACT

A diagnostic catheter and method of use for analyzing tissue is provided. A method for analyzing tissue in accordance with one embodiment of the present invention includes inserting a catheter having a sensor at its distal end into the body of a patient, applying suction through the catheter to secure the tissue to the catheter and then analyzing the tissue with the sensor. An apparatus for analyzing tissue within the body of a patient in accordance with an alternative embodiment of the present invention is also provided. This alternative embodiment includes a catheter having a first end and a second end, the first end having an orifice and a sensor, the catheter also having a lumen.

14 Claims, 3 Drawing Sheets

(56) References Cited

U.S. PATENT DOCUMENTS

| | | |
|---|---|---|
| 5,817,033 A | 10/1998 | DeSantis et al. |
| 5,836,311 A | 11/1998 | Borst et al. |
| 5,842,985 A | 12/1998 | Lundback |
| 5,927,284 A | 7/1999 | Borst et al. |
| 6,035,229 A * | 3/2000 | Silverstein et al. ........... 600/473 |
| 6,081,738 A * | 6/2000 | Hinohara et al. ............. 600/407 |
| 6,157,852 A | 12/2000 | Selmon et al. |
| 6,171,303 B1 * | 1/2001 | Ben-Haim et al. .............. 606/15 |
| 6,174,307 B1 * | 1/2001 | Daniel et al. ..................... 606/15 |
| 6,231,518 B1 | 5/2001 | Grabek et al. |
| 6,237,605 B1 * | 5/2001 | Vaska et al. ................... 128/898 |
| 6,289,229 B1 * | 9/2001 | Crowley ....................... 600/310 |
| 6,311,692 B1 | 11/2001 | Vaska et al. |
| 6,405,732 B1 * | 6/2002 | Edwards et al. .............. 128/898 |
| 6,728,565 B2 * | 4/2004 | Wendlandt .................... 600/407 |
| 2002/0049425 A1 * | 4/2002 | Mosel et al. .................. 604/544 |
| 2002/0173785 A1 * | 11/2002 | Spear et al. ..................... 606/41 |

\* cited by examiner

DIAGNOSTIC CATHETER USING A VACUUM FOR TISSUE POSITIONING

RELATED APPLICATIONS

This application is a continuation of U.S. patent application Ser. No. 09/513,076, which was filed on Feb. 25, 2000 now U.S. Pat. No. 6,728,565, and which is herein incorporated, in its entirety, by reference.

FIELD OF THE INVENTION

The present invention is directed to the analysis of internal tissue of a patient. More particularly the present invention regards the use of a vacuum within a patient's body to secure tissue near a diagnostic sensor.

BACKGROUND OF THE INVENTION

Diagnostic procedures to analyze and diagnose a patient are a common component of modern medical care. There are numerous diagnostic procedures that can be performed on a patient. Some of these diagnostic procedures, such as x-ray and Magnetic Resonance Imaging, are performed completely outside of the body while others, such as tissue biopsies and in situ analysis, require entry into the body and more direct contact with the suspect body part. Those procedures that require more direct tissue contact may be performed through the esophagus and other existing orifices in the patient or through incisions, both small and large, made in the body of the patient.

Whether the diagnostic procedure is performed through an existing orifice or through an incision in the body of the patient, the tissue to be analyzed may often be out of the direct reach of the practitioner. In these situations, in order to reach and analyze the tissue, the practitioner will often employ an instrument having sensors at its distal end. When an instrument is employed the practitioner must manipulate and guide the instrument from outside the body in order to position the sensors, located at its distal end, next to the suspect tissue. This manipulation and steering of the instrument is often a time-consuming and cumbersome process.

For example, when tissue is analyzed during an endoluminal procedure, the practitioner must manipulate the medical instrument containing the sensor within the tight quarters of the endoscope. Once the sensor is properly positioned by the practitioner, it must then be maintained adjacent to the tissue in order to receive satisfactory results. In some circumstances the practitioner may not be able to satisfactorily manipulate the sensor in order to position it near the tissue to be analyzed. Similarly they may not be able to satisfactorily maintain the contact between the tissue and the instrument during the analysis. To resolve both of these problems, a second instrument, having a hook at its distal end, has been employed. This second instrument is inserted down into the endoscope in order to hook the tissue, move it next to the sensor, and hold the tissue in place during the testing. The application of this second instrument, although frequently used, is disfavored as its use is time consuming and can injure and permanently damage the tissue being tested.

In another example, when diagnostic testing is performed without an endoscope, directly through an incision into the patient's body, the practitioner must also position the sensor adjacent to the suspect tissue and may also be required to hold the tissue in direct contact with the catheter in order to perform the analysis. Here, too, positioning the catheter and maintaining its direct contact with the tissue is an arduous and tedious process. A second instrument, such as the hook described above, is often used to grab the tissue, tug it to the sensor and anchor the tissue in direct contact with the catheter. As in the endoluminal procedure, the use of this second instrument, the hook, prolongs the procedure and increases the risk of injury to the tissue.

As is evident, what is needed is a method and an apparatus that provides for the diagnosis of suspect and diseased tissue within the body of a patient without the cumbersome, time-consuming, and risky procedures that have been employed in the past.

SUMMARY OF THE INVENTION

In accordance with the present invention a diagnostic catheter using a vacuum for tissue positioning is provided. A method for analyzing tissue in accordance with one embodiment of the present invention includes inserting a catheter having a sensor at its distal end into the body of a patient, applying suction through the catheter to secure the tissue to the catheter and then analyzing the tissue with the sensor.

An apparatus for analyzing tissue within the body of a patient in accordance with an alternative embodiment of the present invention is also provided. This alternative embodiment includes a catheter having a first end and a second end, the first end having an orifice and a sensor, the catheter also having a lumen.

DETAILED DESCRIPTION

Figure 1:
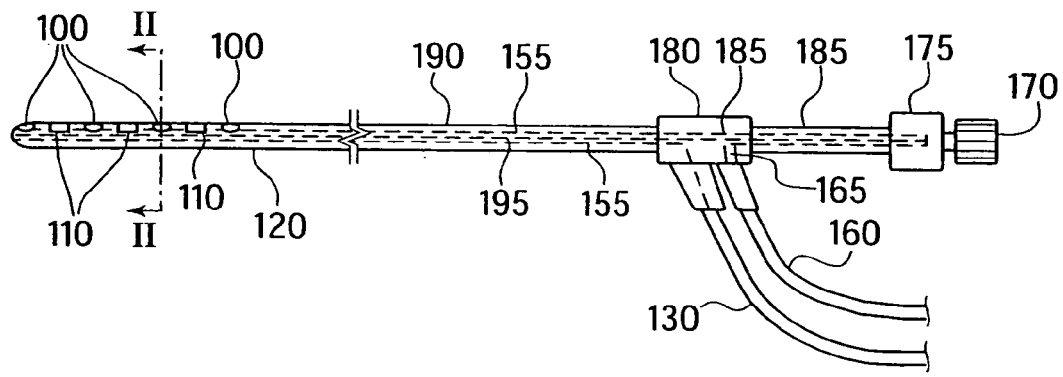
FIG. 1 is a catheter in accordance with a first embodiment of the present invention.

FIG. 1 illustrates a catheter 10 in accordance with a first embodiment of the present invention. This catheter 10, which may be tube-shaped and may have a 2-3 mm external diameter, contains a hollow cylindrical distal tip 120 as well as a hollow cylindrical catheter body 190 and a hollow cylindrical tube 185. The distal tip 120 contains four equally sized orifices 100 along its surface. These orifices 100, which may be 0.5 mm in diameter, penetrate completely through one of the walls of the catheter's 10 hollow cylindrical distal tip 120 and may be spaced a diameter apart from one another. The hollow cylindrical distal tip 120 also contains three sensors 110 affixed to its surface and equally located between the four orifices 100. These sensors 110 may be numerous types of sensors including electrical sensors that test the voltage drop across the tissue being tested, ultrasound sensors, such as the Boston Scientific/SCIMED UltraCross® TX200 transducers, which employ sound waves to analyze the tissue, and optical sensors, which employ visible or non visible light to sense the properties of the tissue being analyzed. These sensors 110 are connected to sensor line 195 which is located within the distal tip 120, the catheter body 190, and the coupler 180. This sensor line 195 connects the sensors 110 with the sensor communication cable 130. The sensor communication cable 130 is in turn connected to a sensor output device (not shown) such as a cathode ray tube. Dependent upon the type of sensors 110 employed the sensor line 195 and the sensor communication cable 130 may be electrical wires, optical fibers, or some other communication link.

As can be seen, a vacuum hose 160 is also connected to the coupler 180. In addition to being connected to the coupler 180 on one end, the vacuum hose 160 is also connected to a vacuum pump, which is not shown, at the other end. This vacuum pump, although not illustrated, may be a 1180 Gomco suction unit, capable of creating a vacuum between 0 and 22 in. Hg and having a bottle coupled to it to prevent solids and liquids from entering the pump. This vacuum pump is used to create an inward suction force through the orifices 100 located at the distal tip 120 of the catheter 10. This inward vacuum force generated by the vacuum travels from the vacuum pump through the vacuum hose 160, through the first vacuum channel 165 located in the coupler 180 and the tube 185, through the suction adjustment valve 175, back through the tube 185, this time in the second vacuum channel 155, which is located within the tube 185, through the coupler 180, the catheter body 190, and the distal tip 120, such that the vacuum force is in fluid communication with the orifices 100.

A suction adjustment knob 170 is rotationally connected to the suction adjustment valve 175. This suction adjustment valve 175 regulates the amount of suction from the vacuum pump (not shown) that will be transferred from the first vacuum channel 165 to the second vacuum channel 155 and eventually to the orifices 100 located in the distal tip 120 of the catheter 10. By turning the suction adjustment knob 170 the suction adjustment valve 175 is opened or closed and the amount of suction drawn through the orifices 100 at the distal tip 120 of the catheter 10 is either concomitantly increased or decreased.

In practice a practitioner utilizing the catheter 10 of FIG. 1 may insert the catheter 10 into the body of the patient through an existing orifice or through an incision made specifically for the procedure. The practitioner would then position the distal tip 120 of the catheter 10, which is made from a flexible polymer, allowing the practitioner to bend and flex the catheter next to the tissue to be diagnosed. Then, once the catheter's 10 distal tip 120 is in its desired position, the practitioner would then turn the vacuum pump on and adjust the amount of vacuum that will be drawn through the orifices 100 at the distal tip 120 of the catheter 10 by turning the suction adjustment knob 170. As the practitioner rotates the suction adjustment knob 170 and increases the vacuum drawn through the four orifices 100, the tissue to be analyzed is drawn towards the orifices 100 and, consequently, towards the sensors 110. Once the suspect tissue has been repositioned and comes in contact with the sensors 110 the strength of the vacuum force may be maintained or it may be reduced by the practitioner to a level sufficient to maintain the contact between the tissue and the sensors 110. By reducing the vacuum force holding the tissue to the sensors 110 the concentrated forces on the tissues are reduced. The distal tip 120 of the catheter 10 and the sensors 110 will remain in contact with the tissue for the duration of the analysis.

Once the requisite analysis and diagnosis has been completed the vacuum may be reduced by turning the suction adjustment knob 170 or by turning the vacuum off, and the tissue will be free to revert back to its original resting position within the body. Once the tissue is released from the orifices 100 the catheter 10 can be removed from the patient or the procedure can be repeated again, as many times as required, for different sections of tissue.

Figure 2:
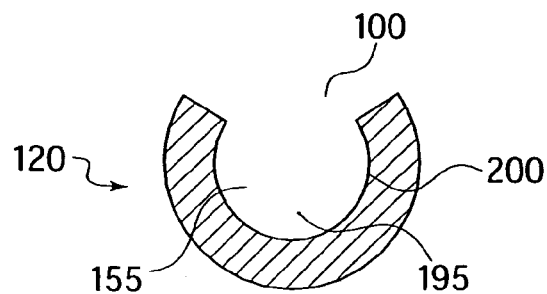
FIG. 2 is a cross-sectional view along line 2-2 of FIG. 1.

FIG. 2 is a cross-sectional view taken along line 2-2 of FIG. 1. As can be seen the distal tip 120 of the catheter 10 has a circular cross-section and the orifice 100 penetrates through the surface and the inner wall 200 of the distal tip 120. The sensor line 195 as well as the second vacuum channel 155 are also evident in FIG. 2.

Figure 3:
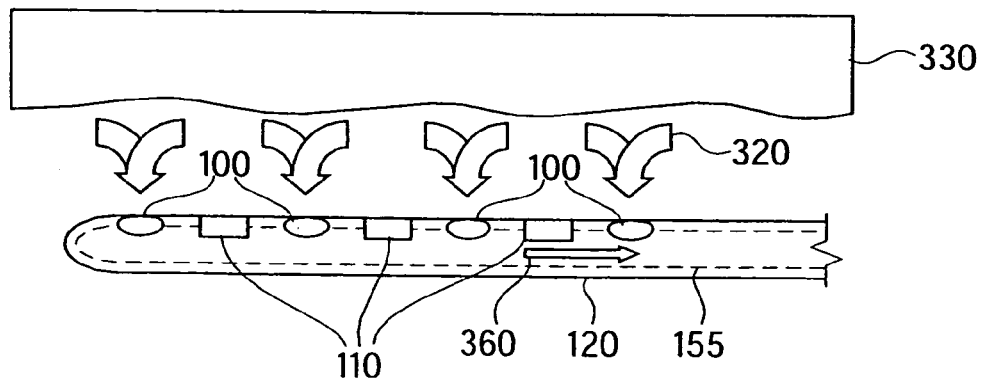
FIG. 3 is an enlarged view of the catheter from FIG. 1 after being placed next to tissue to be analyzed.

FIG. 3 is an enlarged view of the distal tip 120 of the catheter 10 after it has been positioned near a tissue 330 within the body of the patient. Inward force arrows 320 are clearly shown. The inward force arrows 320 highlight the position of the downward force created through the plurality of orifices 100 by the vacuum being drawn through the second vacuum channel 155. The direction of the vacuum force communicated from the vacuum pump through the catheter to the second vacuum channel 155 is illustrated by arrow 360.

In practice, and as discussed above, as the amount of vacuum is increased the tissue 330 is drawn down to the orifices 100 until the tissue 330 meets the sensors 110. The sensors 110, now touching the tissue, analyze the tissue and output their results to sensor electronics, including the cathode ray tube discussed above. Once the requisite data is obtained the vacuum is reduced, the tissue 330 is released, and the catheter may be removed or the procedure can be repeated again on a different area of tissue.

Figure 4:
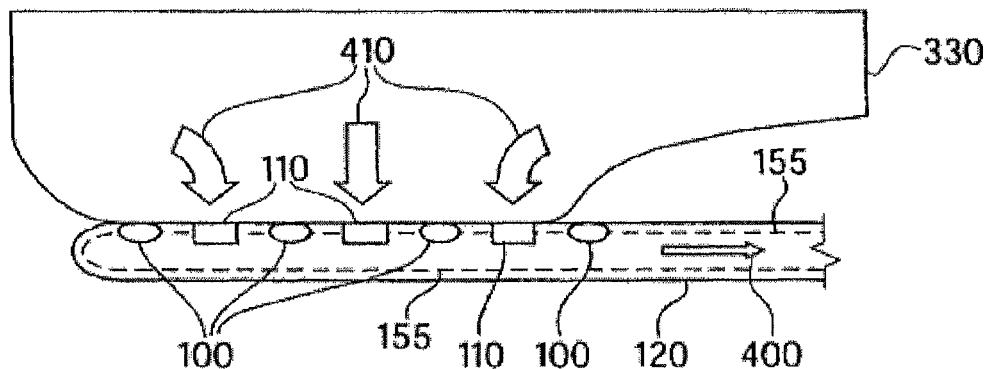
FIG. 4 is an enlarged view of the catheter from FIG. 1 wherein a vacuum force has been used to draw tissue down and in contact with the catheter.

FIG. 4 illustrates the distal tip 120 of the catheter after the suction being drawn down the second vacuum channel 155 has been increased, as shown by arrow 400, the suction now drawing the tissue 330 down and in contact with the sensors 110. The contact points between the sensors 110 and the tissue 330 are highlighted by arrows 410.

Figure 5:
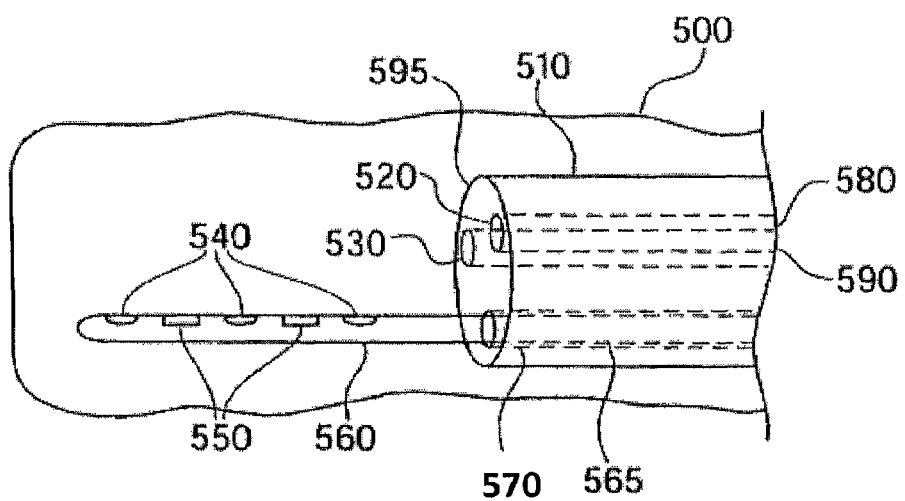
FIG. 5 is the distal end of an endoscope containing a catheter in accordance with a second embodiment of the present invention.

FIG. 5 illustrates the distal end 595 of a second embodiment of the present invention wherein a catheter 565 is inserted into the internal working channel 570 of an endoscope 510. As can be seen, a light tip 520 of a light pipe 580 is located at the distal end 595 of the endoscope 510. This light tip 520 is connected the light pipe 580 which is connected to a light source located at the proximate end of the endoscope (not shown). Also located at the distal end 595 of the endoscope 510 is an optical sensor 530. The optical sensor 530 is connected to a communication line 590 which links the optical sensor 530 to the proximate end of the endoscope 510 (not shown) and allows the images gathered by the optical sensor 530 to be viewed by the practitioner on a nearby display screen. This optical sensor 530 may be used to assist the practitioner in navigating the distal end 595 of the endoscope 510 to the tissue to be analyzed or alternatively it may be utilized to inspect tissue being analyzed by the sensors 550 located on the distal tip 560 of the catheter 565.

As is evident, the catheter 565 is located within the internal working channel 570 of the endoscope 510. The distal tip 560 of the catheter 565 extends from the distal end 595 of the endoscope 510 in this illustration. As in the previous embodiments, the distal tip 560 contains several orifices 540, three in this embodiment, as compared to the four orifices utilized in the embodiment described above. The distal tip 560 also contains two sensors 550 as compared to the three employed in the first embodiment.

A practitioner using this second embodiment would first insert the catheter 565 into the internal working channel 570 at the proximate end (not shown) of the endoscope 510. The catheter 565 would only partially be inserted into the internal working channel of the endoscope 510 such that the distal tip 560 of the catheter 565 would not emerge from the distal end of the endoscope 510 at the beginning of the procedure. Next, the endoscope 510 may be inserted into the body of the patient through an opening, such as the mouth, or through an incision made in the body specifically to accommodate the diagnostic procedure. The endoscope 510 would then be guided into position from outside the body of the patient by the practitioner. If necessary the practitioner may turn the light tip 520 on and use the optical sensor 530 to assist in guiding the distal end 595 of the endoscope 510 down into its desired resting location. Then, once the distal end 595 of the endoscope 510 was positioned near the tissue to be analyzed the practitioner would extend the catheter's 565 distal tip 560 out from inside the internal working channel 570. The practitioner would then position the distal tip 560 to be adjacent to the tissue to be analyzed, the orifices 540, located on the distal tip 560, facing the tissue to be tested. Similar to the positioning of the endoscope, the practitioner may also illuminate the light tip 520 and utilize the optical sensor 530 to aid in properly positioning the distal tip 560 of the catheter 565. Once the distal tip 560 of the catheter 565 is properly positioned, the practitioner would turn on the vacuum source in order to draw the tissue towards the orifices 540. Once the sensors 550 began to adequately sense the tissue, the practitioner could then adjust the vacuum being drawn through the orifices, either at the source of the vacuum or at the catheter 565 through an adjustment valve (illustrated above), so that only the requisite amount of force was utilized to maintain contact between the sensors 550 and the tissue being analyzed.

Now coupled to the distal tip 560 of the catheter, the tissue, in addition to being analyzed by the sensors 550, may also be manipulated by the practitioner by moving the catheter at its proximate end (not shown). As required, the tissue may be manipulated within the view of the optical sensor 530. Once the required data was obtained by the sensors 550, the vacuum would be reduced until the tissue would be released from the orifices 540. If additional tissue testing was required, the procedure would be repeated. Once the requisite testing was completed the distal tip 560 of the catheter 565 would be withdrawn back into the endoscope 510 so that it no longer extended outside of the endoscope 510. The endoscope 510 would then be removed from the body.

While a light 520 and an optical sensor 530 are shown at the end of the endoscope 510 other diagnostic components can also be placed at the end of the endoscope 510 to assist the practitioner. For example, the same electrical and ultrasonic sensors placed on the surface of the distal tip 560 of the catheter may also be placed on the distal end 595 of the endoscope 510 to provide additional sources of data to the practitioner during the diagnosis.

Figure 6:
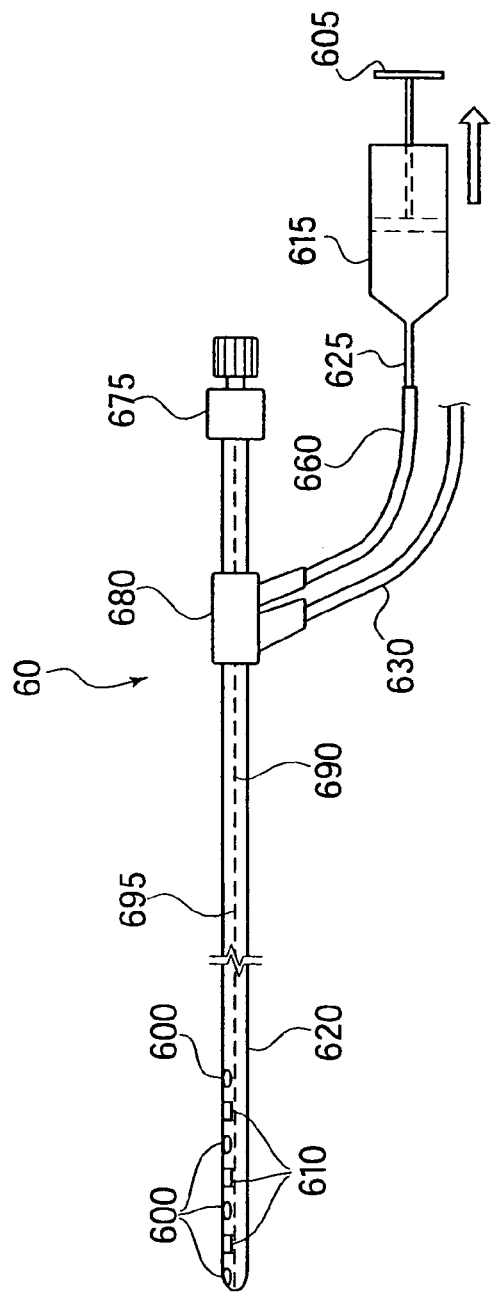
FIG. 6 is a catheter employing a syringe to create a vacuum force in accordance with a third embodiment of the present invention.

FIG. 6 illustrates a catheter 60 in accordance with a third embodiment of the present invention. In FIG. 6 the catheter 60 has a catheter body 690 containing a sensor line 695. The catheter body 690 is rigidly connected to a coupler 680. The coupler 680 has a sensor communication cable 630 and a vacuum hose 660 protruding from the coupler's 680 lower side. The vacuum hose 660 has a connection hose 625 sealably connected to the vacuum hose 660. The connection hose 625 is sized to fit to the connection hose 625 on one side and to a syringe 615 on the other. The syringe 615 is in fluid communication with the orifices 630 via the connection hose 625, the vacuum hose 660, the coupler 680, and the catheter body 690. The syringe 615 contains a plunger 605. When the plunger 605 is drawn out, in the direction of the arrow, it creates a vacuum force that is ultimately transferred to the orifices 600 at the distal tip 620 of the catheter 60. This syringe 615 is, therefore, an alternative to the vacuum pump described in the previous embodiments. When the syringe 615 is used, the vacuum adjustment valve 675 would be rotated until it was completely open so that the practitioner would be controlling the amount of vacuum force generated at the orifices 600 of the catheter 60 by sliding and holding the plunger 605 of the syringe 615.

Figure 7:
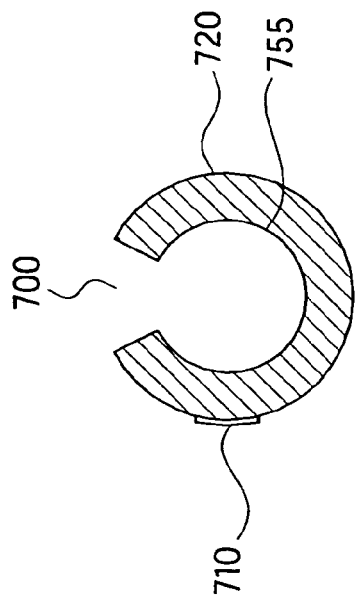
FIG. 7 is a cross-sectional view of the distal end of a catheter in accordance with a fourth embodiment of the present invention.

Alternatively, as illustrated in FIG. 7, which is a cross-sectional view through the distal end of a fourth embodiment of the present invention, the sensors 710 and the orifices 700 do not need to be in line with one another along the outside surface of the catheter. Instead, they may also be placed at different locations of the distal tip 720 of the catheter. For example, as is evident in FIG. 7 the orifice 700 penetrates through the top of the outside surface of the distal tip 720 of the catheter while the sensor 710 is positioned along a side of the outside surface of the distal tip 720 of the catheter. Similarly, while the sensors are illustrated on the surface of the catheter they may instead be formed in the catheter or placed on the inside wall 755 of the distal tip 720 of the catheter. Also, while an endoscope is described in the embodiments above, a flexible tube creating a pathway may, instead, be used in its place. Therefore, as will be evident to one of skill in the art, the above embodiments are merely illustrative of the invention disclosed herein and other embodiments may be employed without departing from the spirit and scope of the present invention.

What is claimed is:

1. A method of analyzing tissue within the body of a patient comprising:
   inserting an endoscope having a distal end through a natural body orifice and into a body lumen in natural communication with the natural body orifice, the endoscope comprising a working channel extending longitudinally therethrough, wherein the distal end of the endoscope contains an optical sensor;
   inserting a catheter into the working channel of the endoscope,
      the catheter having a sensor at a distal end and a catheter orifice through and flush with an external peripheral surface of the catheter,
      the catheter orifice being proximate to the sensor;
   applying a vacuum force through the catheter orifice to secure a portion of tissue to be analyzed flush with the external peripheral surface of the catheter and adjacent to the sensor of the catheter, wherein the tissue to be analyzed defines the body lumen;
   analyzing the tissue with the sensor of the catheter;
   manipulating the catheter, with the portion of the tissue secured on the external peripheral surface of the catheter by the vacuum force through the catheter orifice, to move the tissue towards the distal end of the endoscope; and
   viewing the tissue using the optical sensor.

2. The method of claim 1 further comprising:
   reducing the vacuum force applied through the catheter orifice while maintaining the tissue flush with the external peripheral surface of the catheter.

3. A method of analyzing tissue within the body of a patient comprising:
   inserting an endoscope having a distal end through a natural body orifice and into a body lumen in natural communication with the natural body orifice, the endoscope comprising a working channel extending longitudinally therethrough, wherein the distal end of the endoscope contains a sensor;
   inserting a catheter having a sensor and a catheter orifice in the working channel of the endoscope;

extending the catheter from the distal end of the endoscope to a position adjacent to a preselected tissue to be analyzed, wherein the tissue to be analyzed defines the body lumen;

positioning the catheter orifice adjacent to the preselected tissue to be analyzed, the catheter orifice flush with an external peripheral surface of the catheter;

applying a vacuum force to the tissue via the catheter to secure the tissue into a predetermined sensing position relative to the sensor of the catheter, wherein at least a portion of the tissue is positioned flush with the external peripheral surface of the catheter and adjacent the sensor of the catheter;

analyzing the tissue with the sensor of the catheter;

manipulating the catheter, with the tissue secured on the external peripheral surface of the catheter by the vacuum force through the catheter orifice, to move the tissue into a predetermined viewing position relative to the sensor of the endoscope; and viewing the tissue using the sensor of the endoscope.

4. The method of claim 3 wherein the force is applied to the tissue with a negative pressure created through the catheter orifice.

5. The method of claim 4 further comprising:

illuminating the tissue secured to the catheter with a light located on the endoscope; and wherein the sensor of the endoscope is an optical sensor.

6. A method of analyzing tissue within the body of a patient comprising:

inserting an endoscope having a distal end through a natural body orifice and into a body lumen in natural communication with the natural body orifice, the endoscope comprising a working channel extending longitudinally therethrough, wherein the distal end of the endoscope contains a sensor;

inserting a catheter having a sensor into the working channel;

positioning the distal end of the endoscope at a first predetermined position adjacent to tissue to be tested, wherein the tissue to be tested defines the body lumen;

extending the catheter out of the distal end of the endoscope and positioning the catheter at a second predetermined position adjacent to tissue to be tested;

applying suction through a catheter orifice located through and flush with an external peripheral surface of the catheter and proximate to the sensor of the catheter to secure a first portion of the tissue flush with the external peripheral surface of the catheter and adjacent the sensor of the catheter; and analyzing the first portion of the tissue with the sensor of the catheter;

manipulating the catheter, with the first portion of the tissue secured on the external peripheral surface of the catheter by the suction applied through the catheter orifice, to move a second portion of the tissue toward the distal end of the endoscope; and analyzing the second portion of the tissue using the sensor of the endoscope.

7. The method of claim 1, wherein analyzing the tissue with the sensor includes disposing the sensor in direct contact with the tissue.

8. The method of claim 3, wherein extending the catheter from the distal end of the endoscope includes positioning a side surface of the catheter, with the catheter orifice, to face toward a central longitudinal axis of the endoscope.

9. The method of claim 6, wherein applying suction through the catheter orifice includes applying suction through an adjacent catheter orifice, the catheter orifice and the adjacent catheter orifice being positioned on substantially opposing sides of the sensor of the catheter.

10. The method of claim 1, wherein the catheter orifice is a first catheter orifice, the catheter includes a second catheter orifice, the sensor of the catheter is an optical sensor between the first and second catheter orifices, and the vacuum force is applied through the first and second catheter orifices to secure the portion of tissue to be analyzed flush with the external peripheral surface of the catheter and adjacent to the optical sensor of the catheter.

11. The method of claim 3, wherein:

the sensor of the catheter is one of a plurality of optical sensors, the catheter orifice is one of a plurality of catheter orifices, the catheter orifices are positioned adjacent to the preselected tissue to be analyzed, the catheter orifices flush with the external peripheral surface of the catheter, and the force is applied to the tissue via the catheter orifices of the catheter to secure the tissue into the predetermined sensing position relative to the optical sensors, with at least a portion of the tissue positioned flush with the external peripheral surface of the catheter and adjacent the optical sensors.

12. The method of claim 11, wherein the optical sensors and catheter orifices alternate along the external peripheral surface of the catheter.

13. The method of claim 6, wherein:

the sensor of the catheter is one of a plurality of optical sensors, the catheter orifice is one of a plurality of catheter orifices located through and flush with the external peripheral surface of the catheter and proximate to the optical sensors, suction is applied through the plurality of catheter orifices to secure the portion of the tissue flush with the external surface of the catheter and adjacent the optical sensors, and the tissue is analyzed with the optical sensors located on the catheter.

14. The method of claim 13, wherein the optical sensors and the catheter orifices alternate along the external peripheral surface of the catheter.

\* \* \* \* \*